US009993253B2

(12) United States Patent
Furey et al.

(10) Patent No.: US 9,993,253 B2
(45) Date of Patent: Jun. 12, 2018

(54) DISPENSING DEVICE AND METHOD FOR DELIVERING FILAMENTARY MATERIAL INTO A PATIENT (71) Applicants: Cook Medical Technologies LLC, Bloomington, IN (US); Cook Biotech Incorporated, West Lafayette, IN (US)

(72) Inventors: Aidan Furey, Valby (DK); Steen Aggerholm, St. Heedinge (DK); Palle Munk Hansen, Vemmedrup (DK); Anders Ginge Jensen, Hornslet (DK); Kirsten Asser Larsen, Moerkoev (DK); Ryan Bernstein, Lafayette, IN (US)

(73) Assignees: Cook Medical Technologies LLC, Bloomington, IN (US); Cook Biotech Incorporated, West Lafayette, IN (US)

( * ) Notice: Subject to any disclaimer, the term of this patent is extended or adjusted under 35 U.S.C. 154(b) by 245 days.

(21) Appl. No.: 14/732,420

(22) Filed: Jun. 5, 2015

(65) Prior Publication Data
US 2015/0351773 A1    Dec. 10, 2015

Related U.S. Application Data (60) Provisional application No. 62/008,085, filed on Jun. 5, 2014.

(51) Int. Cl.
A61M 29/00    (2006.01)
A61B 17/12    (2006.01)
(Continued)

(52) U.S. Cl.
CPC .... *A61B 17/12113* (2013.01); *A61B 17/1214* (2013.01); *A61B 17/12031* (2013.01);
(Continued)

(58) Field of Classification Search
CPC .............. A61B 17/12; A61B 17/12113; A61B 17/12109; A61B 17/12131;
(Continued)

(56) References Cited

U.S. PATENT DOCUMENTS 5,021,059 A    6/1991    Kensey et al.
5,263,927 A    11/1993   Shlain
(Continued)

FOREIGN PATENT DOCUMENTS

EP    0743047 A2    11/1996
EP    2 361 567 A1    8/2011
(Continued)

*Primary Examiner* — Victor Nguyen
(74) *Attorney, Agent, or Firm* — Woodard, Emhardt, Moriarty, McNett & Henry LLP (57) ABSTRACT There are disclosed various dispensing mechanisms for dispensing filamentary material (24) through a catheter (12) into a treatment site of a patient, for example into an aneurysm sack (20) in a patient's vessel (22). In one embodiment the assembly (100) includes a conical material carrier (150) which is substantially aligned with the dispensing direction, thereby avoiding the need to have a rotating carrier. Another embodiment has a carrier (340) which is at least partially cylindrical. The carrier (150, 340) provides for efficient dispensation of filamentary material at substantial dispensing speeds.

42 Claims, 9 Drawing Sheets (51) Int. Cl.
*A61F 2/82* (2013.01)
*A61F 2/90* (2013.01)
*A61B 17/00* (2006.01)
*A61B 90/00* (2016.01)

(52) U.S. Cl.
CPC ............... *A61B 17/12118* (2013.01); *A61B 2017/00004* (2013.01); *A61B 2017/00539* (2013.01); *A61B 2017/1205* (2013.01); *A61B 2090/032* (2016.02); *A61F 2/82* (2013.01); *A61F 2/90* (2013.01); *A61F 2002/823* (2013.01)

(58) Field of Classification Search
CPC ........ A61B 17/12186; A61B 17/12031; A61B 17/1214; A61M 29/00
See application file for complete search history.

(56) References Cited

U.S. PATENT DOCUMENTS

| | | | |
|---|---|---|---|
| 5,911,731 | A | 6/1999 | Pham et al. |
| 6,093,179 | A | 7/2000 | O'Hara et al. |
| 6,296,632 | B1 | 10/2001 | Luscher et al. |
| 6,299,590 | B1 | 10/2001 | Luscher et al. |
| 6,312,421 | B1 | 11/2001 | Boock |
| 6,440,098 | B1 * | 8/2002 | Luscher ........... A61B 17/12022 604/13 |
| 6,589,199 | B1 | 7/2003 | McCrory et al. |
| 6,629,947 | B1 | 10/2003 | Sahatjian et al. |
| 2003/0036712 | A1 | 2/2003 | Heh et al. |
| 2005/0033323 | A1 | 2/2005 | Kim |
| 2006/0147483 | A1 | 7/2006 | Chaouk et al. |
| 2010/0042117 | A1 | 2/2010 | Kim et al. |
| 2014/0148791 | A1 | 5/2014 | Barker, Jr. et al. |
| 2015/0351773 | A1 | 12/2015 | Furey et al. |
| 2017/0100129 | A1 | 4/2017 | Furey et al. |

FOREIGN PATENT DOCUMENTS

| | | |
|---|---|---|
| WO | WO 1996/004954 A1 | 2/1996 |
| WO | WO 1999/011191 A1 | 3/1999 |
| WO | WO 1999/11191 A1 | 3/1999 |
| WO | WO 2004/098420 A2 | 11/2004 |

* cited by examiner

DISPENSING DEVICE AND METHOD FOR DELIVERING FILAMENTARY MATERIAL INTO A PATIENT

REFERENCE TO RELATED APPLICATION

This application claims the benefit of U.S. Provisional Application No. 62/008,085, filed Jun. 5, 2014, which is hereby incorporated by reference.

TECHNICAL FIELD

The present invention relates to apparatus and a method for delivering filamentary material into a patient, in the preferred embodiments to delivery of material endoluminally through a percutaneous entry point. The preferred embodiments can be used for filling an aneurysm, for closing a vessel or other organ, as well as for other medical treatments.

BACKGROUND ART

There are several medical conditions which can benefit from implantation into a patient of a filler material, an embolization or other device, whether temporary or permanent. Examples include the closure of blood vessels or other lumens so as to occlude these. Another example for which such procedures can be particularly useful is in the treatment of aneurysms, where a part of a vessel wall weakens and then expands outwardly to create an enlarged zone of the vessel, often having the form of a sac. This vessel expansion occurs as a result of blood pressure and tends to continue due to further and progressive weakening of the vessel wall. If left untreated, persistent pressure from the blood flow on the weakened wall tissue can lead to eventual rupture of the vessel and consequential haemorrhaging. Treatments for aneurysms have therefore focused on reducing the pressure on the weakened vessel wall, for instance by diverting blood flow or by isolating the weakened vessel wall, for instance by means of a stent graft. Another treatment method involves filling the aneurysm sac with a filler material which stops the flow of blood into the sac and therefore stops or substantially reduces the pressure on the weakened walls. The filler may be an embolization coil, which will cause blood therearound to clot and thus close the sac and provide a protective barrier to prevent vessel rupture. In other instances, the aneurysm may be filled with a biocompatible material, such as a hydrogel or a polysaccharide fibre, which may be of a biodegradable nature. A biodegradable filler performs the same function as an embolization coil, that is to fill the aneurysm sac and provide pressure protection to the weakened vessel walls, with the additional advantage of allowing remodeling of the vessel wall over time. Moreover, biodegradation of the filler will ensure that no foreign matter remains in the patient's vessel after conclusion of the treatment.

Such fillers and coils can also be used to close off a vessel or other lumen in a patient.

The process of introducing such a filler or coil into a patient can take time, particularly given that this is often carried out remotely from the aneurysm by an endoluminal procedure.

Examples of prior art devices and methods can, for instance, be found in U.S. Pat. No. 6,312,421, US-2006/0147483, U.S. Pat. No. 6,589,199, U.S. Pat. No. 6,440,098.

SUMMARY

The present invention seeks to provide an improved apparatus for delivering filamentary material into a patient and in the preferred embodiments into a vessel or aneurysm sac.

According to an aspect of the present invention, there is provided apparatus for delivering filamentary material into a patient including: a tubular delivery element having a proximal end, a distal end and a lumen extending within the tubular delivery element from the proximal to the distal ends; a material receptacle having an aperture for receiving driving fluid into the receptacle, and an outlet coupled to the lumen of the tubular delivery element, the outlet extending in a material dispensing direction of the receptacle; a carrier element for carrying filamentary material, the carrier element having an axis substantially aligned with the material dispensing direction of the receptacle and including a body portion around which filamentary material can be wound.

The carrier element is able to support filamentary material wound thereon and to allow unwinding of the material along the axis of the carrier, which does not require the carrier to rotate. The apparatus therefore need not have any moving parts, although in some embodiments it is not excluded that the carrier may be rotatable about its longitudinal axis. The carrier is preferably substantially aligned with the longitudinal axis of the receptacle.

The tubular delivery element may be or include at least one of a catheter, a cannula and a needle.

In the preferred embodiments, the carrier element is precisely aligned with the dispensing direction of the receptacle. In other embodiments, the carrier element is disposed at an angle to the dispensing direction of the receptacle. In such embodiments, the carrier will have a side relatively remote from the outlet of the receptacle and thus to the dispensing direction. This angle is advantageously no more than around 30 degrees relative to the dispensing direction, in practice the longitudinal axis of the receptacle as determined by the direction of movement of the fibre out of the outlet. More suitably, this angle is less than around 20 degrees and even more suitably less than around 10 degrees. In practice, the angle should preferably be less than around 5 degrees.

Preferably, the body portion of the carrier element is generally round in transverse cross-section.

In one embodiment, at least a part of the body portion of the carrier element has a generally conical form tapering in a direction towards the outlet. In this embodiment, the body portion of the carrier element may be conical or frustoconical. Such a form can provide virtually no impediment to unwinding of material from the carrier during dispensation.

The body portion of the carrier element may include a generally cylindrical portion. In one embodiment the body portion of the carrier element includes a conical portion and a generally cylindrical portion extending longitudinally beyond a narrow end of the conical portion.

In the preferred embodiments, the carrier element includes at least one driving fluid conduit, advantageously which includes at least one aperture disposed at an end of the carrier element furthest from the receptacle outlet.

The driving fluid will thus be provided upstream of the wound material, which will assist in its unwinding.

Preferably, the receptacle includes a tapering internal wall adjacent the outlet. The tapering wall, which is most preferably of conical form, will concentrate the flow of driving fluid and increase the speed thereof into the catheter, thereby increasing the speed of dispensation of the material.

The apparatus may include a guiding element at an end of the material carrier closest to the outlet, the guiding element in some embodiments being in the form of an annular guide element. The guiding element can assist in the unwinding of the material and feeding of the material to the receptacle outlet. In some embodiments, the guiding element may be a rotating ring of low friction material, such as a low friction polymer, preferably including a hole for the passage of filamentary material therethrough.

In the preferred embodiment, the material may be small intestine submucosa (SIS), polysaccharide, a biocompatible polymeric thread or other biocompatible material. Specific examples, though the disclosure herein is not limited to these, include: woven polyester (e.g. DACRON®), polyamide (e.g. Nylon), expanded polytetrafluoroethylene (ePTFE; e.g. GORE-TEX®); bioremodelable materials such as: extracellular matrix material (ECM) for instance submucosa, renal capsule membrane, dermal collagen, dura mater, pericardium, fascia lata, serosa, peritoneum and basement membrane layers. Examples of submucosa include: intestinal submucosa, including small intestinal submucosa, stomach submucosa, urinary bladder submucosa and uterine submucosa.

Advantageously, filamentary material is wound on the material carrier from a distal end thereof to a proximal end thereof, the proximal end being closest to the outlet. Preferably, the filamentary material is wound on the material carrier in sections from the distal end to the proximal end. More preferably, the filamentary material is wound on the material carrier in sections up to a maximum wound diameter on the material carrier from the distal end to the proximal end. In the preferred embodiment the filamentary material is wound first at the distal end of the carrier until at least a part of this reaches a wound diameter around that of the desired maximum diameter of wound material on the carrier, and then the winding continues at a position closer to the proximal end, until the desired diameter is attained at that position, with winding continuing at a next position yet closer to the proximal end, and so on until sufficient material has been wound on the carrier. It is preferred that the material is wound in conical layers on the carrier.

The receptacle may be at least partially transparent or translucent. The apparatus may include a fluid supply and pump for pumping driving fluid into the receptacle, the pump optionally including a syringe.

According to another aspect of the present invention, there is provided a carrier for carrying filamentary material deliverable into a patient, the carrier an elongate body portion having a distal end and a proximal end; and filamentary material wound around the body portion, the filamentary material being wound from the distal end of the carrier to the proximal end of the carrier.

Advantageously, the filamentary material is wound on the material carrier in sections from the distal end to the proximal end, preferably in sections up to a maximum wound diameter on the material carrier.

Most preferably, the filamentary material is wound in conical layers on the carrier.

The filamentary material may be any of the materials or combination of materials disclosed herein.

In an embodiment, the carrier includes a receptacle fixing element attached to or integral with the distal end thereof. The receptacle may be a closure element.

According to another aspect of the present invention, there is provided apparatus for delivering filamentary material into a patient, including a receptacle provided with an internal chamber for holding filamentary material, an aperture for receiving driving fluid into the chamber, an outlet through which filamentary material can pass from the chamber, and a pressure sensitive valve associated with the receptacle, the pressure sensitive valve being closed when the pressure of driving fluid is below a threshold and open when the pressure of driving fluid is above the threshold, the pressure sensitive valve when open allowing fluid flow through the chamber and dispensation of filamentary material from the outlet.

The pressure sensitive valve can ensure that driving fluid is supplied at a sufficient pressure to drive filamentary material through the catheter with minimal use of driving fluid.

Preferably, the pressure sensitive valve is disposed at at least one of the inlet and the outlet.

The valve may include at least one resilient valve leaf deformable when fluid pressure thereon exceeds the threshold.

Advantageously, the valve is domed to provide one-way fluid flow therethrough.

Other features of the apparatus and method disclosed herein will become apparent from the following specific description of preferred embodiments.

BRIEF DESCRIPTION OF THE DRAWINGS

Embodiments of the present invention are described below, by way of example only, with reference to the accompanying drawings, in which.

DETAILED DESCRIPTION

There are described below various embodiments of apparatus for feeding filamentary material into a patient. The teachings herein are particularly useful for feeding blocking material into an aneurysm sac of a weakened vessel, so as to close off the aneurysm sac to blood flow and blood pressure.

The apparatus can also be used to supply material to occlude a vessel, for example. The material can be of a type which permanently remains in the patient, thus as a permanent closure or occlusion device, or may be bioresorbable or biodegradable, allowing tissue remodeling over time. In the case of aneurysm treatment, once pressure is removed from within the aneurysm sac the weakened wall tissue can remodel and often will heal fully. In such cases, it is not necessary to maintain a sac filler.

The material is preferably of filamentary form, more particularly as a single or multi strand filament, typically of substantial length. The filamentary material is advantageously of a single length and such that the entire volume of material carried on the material carrier can be delivered by the device into a patient in a single operation. The material could be described as being of thread form.

Figure 1:
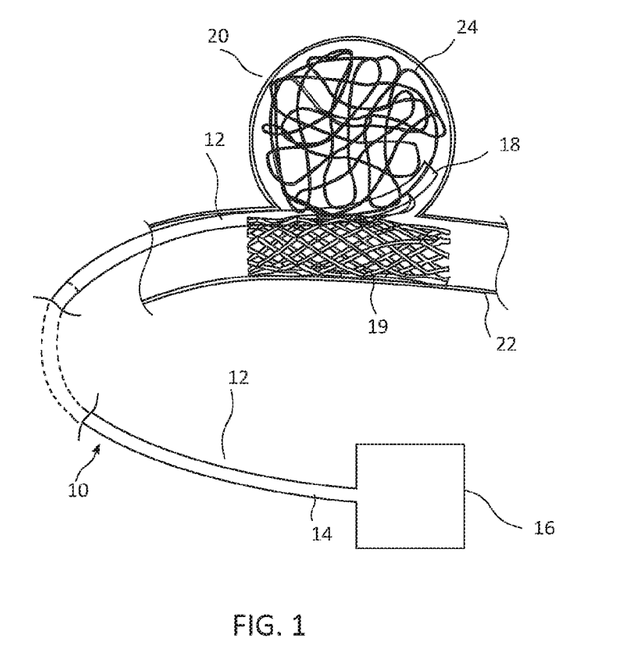
FIG. 1 is a schematic diagram of an embodiment of material feed apparatus according to an embodiment of the invention.

Referring to FIG. 1, there is shown in schematic form a material dispensing assembly 10 incorporating the features of the embodiments disclosed herein. The dispensing assembly 10 includes a catheter 12 having a proximal end 14 coupled to a material receptacle 16, described in further detail below, and a distal end 18 which is fed endoluminally through the vasculature of the patient up to the treatment site, into the sac 20 of an aneurysm formed in a blood vessel 22. The apparatus 10 is designed to dispense into the aneurysm sac 20 filamentary material 24 from the material receptacle 16 through the lumen of the catheter 12. The material dispensed can be any biocompatible material including biocompatible polymeric thread, polysaccharide or other suitable material. Other examples are SIS (small intestine submucosa). Specific examples, though the disclosure herein is not limited to these, include: woven polyester (e.g. DACRON®), polyamide (e.g. Nylon), expanded polytetrafluoroethylene (ePTFE; e.g. GORE-TEX®); bioremodelable materials such as: extracellular matrix material (ECM) for instance submucosa, renal capsule membrane, dermal collagen, dura mater, pericardium, fascia lata, serosa, peritoneum and basement membrane layers. Examples of submucosa include: intestinal submucosa, including small intestinal submucosa, stomach submucosa, urinary bladder submucosa and uterine submucosa.

The distal end of the catheter 12 is typically fed into the aneurysm sac through a stent 19, which may be a braided stent or any other known stent structure. The stent 19 not only positions the distal end 18 of the catheter but also holds the filamentary material in the aneurysm sac.

The filamentary material 24 is intended to fill at least a significant part of the volume of the aneurysm sack 20 so as to stop the flow of blood into the aneurysm 20 and as a result reduce the pressure of blood on the weakened vessel walls of the aneurysm. In the case of a bioresorbable or bioabsorbable material, this will eventually be resorbed or absorbed, typically after a sufficient period which allows recovery of the weakened vessel wall and remodeling of the vessel. In other cases the fibrous material remains permanently within the aneurysm sac, effectively closing this off.

The fibrous material is typically provided as a thin thread or element, for which a substantial length is dispensed from the distal end 18 of the catheter 12 into the aneurysm sac 20 during the deployment procedure. For this purpose, and as described below, the material receptacle 16 includes substantial lengths of filamentary material and held within the material receptacle 16 in such a manner that the material can be reliably and quickly dispensed from the receptacle 16 to the distal end 18 of the catheter 12 and into the treatment site. A preferred example of a thread winding method is described below.

The driving fluid for driving material 18 from the receptacle 16 through the catheter 12 can be provided by a syringe coupled to an inlet to the receptacle, although in other embodiments any other suitable fluid pump may be used.

It is to be understood that the device 10 shown in FIG. 1 could be used in other medical procedures, including, for example, for occlusion of blood vessels, for delivery of filamentary material for other medical applications and so on.

Figure 2:
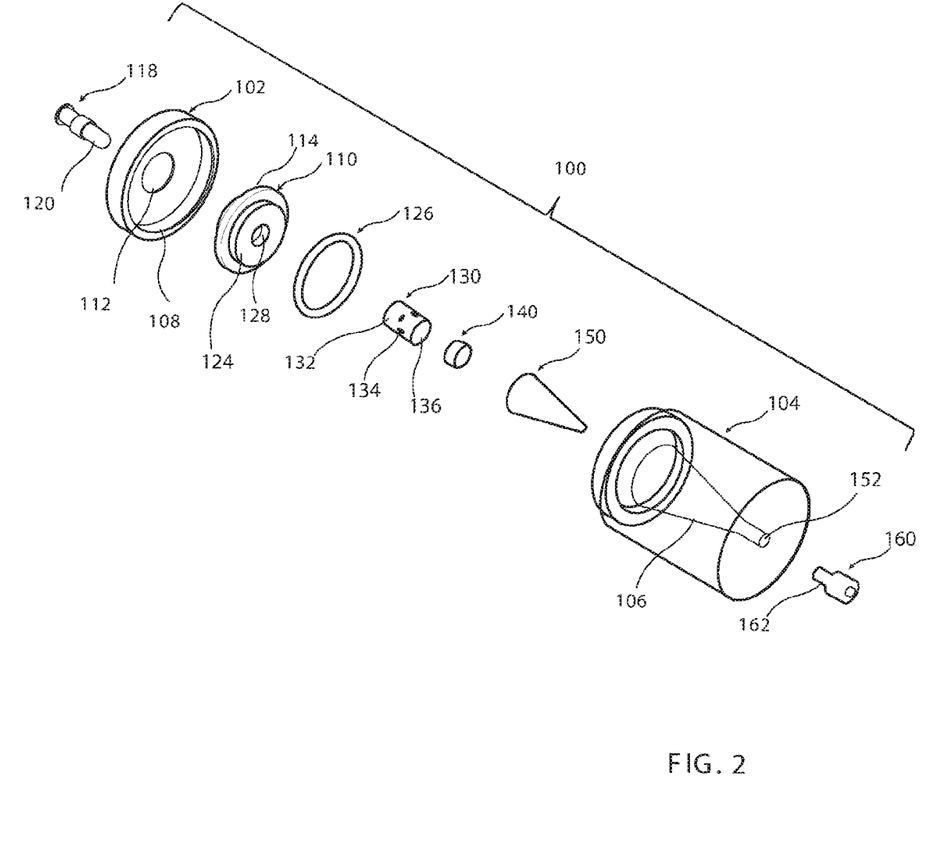
FIG. 2 is a side elevational view of an embodiment of material receptacle in exploded form.

FIGS. 2 to 5 show a first structure of material dispensing assembly 100 for use as the receptacle 16 of FIG. 1. FIG. 2 shows the assembly 100 in exploded view so that the principal components can be readily seen.

With reference to FIG. 2, the assembly 100 includes first and second casing parts 102, 104 which can be secured to one another, for example by means of male and female threaded couplings.

The casing formed by the parts 102, 104 has in this embodiment a cylindrical outer form and, as will be explained in further detail below, a conical internal wall 106 in the larger casing part 104.

The assembly 100 also includes a base or support element 110 which is generally round in plan and in use resides within a rounded recess 108 of the casing part 102. The base element 110 also includes a rounded coupling end 114 which fits within a round aperture 112 of the casing part 102. The rounded coupling end 114 includes an internal bore with a female screw thread (not shown) which co-operates with a male screw threaded element 120 of a luer fitting 118. The base element 110 may be rotatable within the casing part 102 but in other embodiments may be fixed to the casing part, for example by bonding, welding, by a friction fit or locking element of suitable form (for example a key and associated recess). The base element 110 also includes an raised seal support 124 which provides an annular shoulder for holding an O-ring seal 126. The seal support 124 has a central round opening 128, aligned with the threaded bore of the rounded coupling end 114 and in fluid communication therewith. The proximal end 132 of a sleeve 130 fits within the round opening 128 of the base element 110, fixed preferably by a friction fit, by bonding or welding, for example. The sleeve 130 has a plurality of apertures 134 disposed circumferentially around the sleeve at a mid-portion thereof. The distal end 136 of the sleeve 130 is closed by a rounded closure element 140, which is a tight fit within the distal end 136 of the sleeve 130, although may in the alternative or additionally be bonded or welded to the sleeve. The arrangement is such that a fluid passage exists through the luer fitting 118, the base element 110 and the sleeve 130, exiting through the openings 134.

Attached to the closure element 140 is a conical material carrier 150. It is to be appreciated that the material carrier 50 could be formed as a unitary component with the closure element 140, but in other embodiments may be bonded, welded or otherwise fixed to the closure element 140.

The casing part 104 includes an outlet 152 having an internal screw thread which co-operates with a male screw threaded element 162 of a female luer connector 160.

Most of the components of the assembly 100 shown in FIG. 2 may be made of a plastics material, although in the embodiments shown the sleeve 130 is usefully made of a metal, which will be able to affect a friction fit with the components 110, 140 to which it connects.

Figure 3:
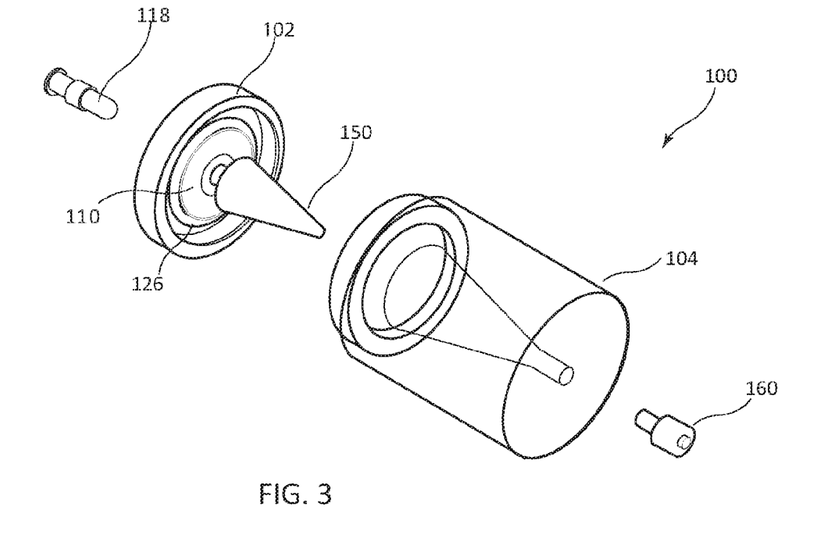
FIG. 3 is a view of the assembly of FIG. 2 in partially assembled form.

Referring now to FIG. 3, this shows the components of FIG. 2 in substantially assembled form. As can be seen, the casing part 102 includes the O-ring seal 126 and the conical material carrier 150, the latter being spaced from the base support 110 by a section of the length of the sleeve 130, specifically by at least the zone of the apertures 134, such that a fluid path exists between the base element 110 and the conical material support 150.

Figure 4:
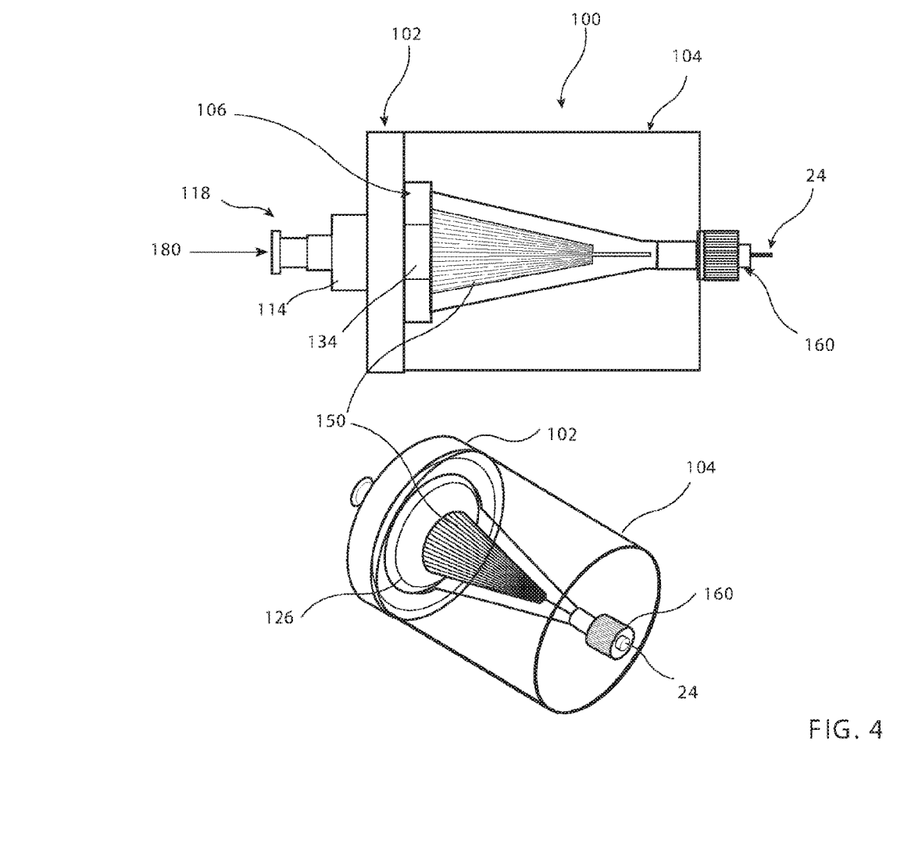
FIG. 4 shows two views of the assembly of FIGS. 2 and 3 in schematic form, on which filamentary material is wound.

Referring now to FIG. 4, this shows the assembly of FIG. 2 in fully assembled form and loaded with filamentary material. The casing parts 102, 104 are shown connected together, with the O-ring seal 126 sealing the chamber 106 formed by the internal walls of the parts 102, 104 in fluid tight manner, save for the inlets and outlets to the assembly. As can be seen, a length of filamentary material 24 is wound around the conical material carrier 150, preferably in a direction from the wide end of the conical carrier 150 to its narrow end, although the direction of winding and number of winding layers may differ from one implementation to another. The free end of the filamentary material 24 passes through the lumen of the outlet 152 and of the female luer connector 160, to exit the assembly 100. The material 24 will pass into a catheter 12 attached to the female luer connector 160, in the manner shown in FIG. 1. The male luer connector 118 attached to the inlet to the dispending assembly 100 connects to a source 180 of driving fluid (not shown in FIG. 4), which may be a pump such as a syringe.

The filamentary material 24 is preferably of a diameter which is a close fit within the catheter 12. When driving fluid, typically saline solution, is pumped into the dispenser assembly 100 through the inlet luer connector 118, this will pass into the chamber 106 of the assembly 110 through the apertures 134 of the sleeve 130. Continued flow of driving fluid will then cause the driving fluid to flow out of the outlet 152 and female luer connector 160, in practice into a catheter 12 attached to the female luer connector 160. This driving fluid will pull the filamentary material 24 with the fluid flow, effectively dispensing the filamentary material 24 from the dispensing assembly 100. The material will unwind from the conical material carrier 150 during the dispensing operation. It is preferred, as described above, that the material carrier 150 is fixed in position, although in some embodiments it may be rotatably attached to the casing portion 102, in which case the carrier 150 will rotate as the filamentary material 24 unwinds therefrom.

The dispensing procedure will typically continue until there is no more filamentary material to dispense. It will be appreciated that in this case, there will be provided a length of filamentary material deemed sufficient and required for the particular medical condition. It is not excluded, however, that the dispensing operation could be terminated once the physician has determined that a sufficient of length or volume of filamentary material has been deployed at the treatment site, for example that an aneurysm sac has been filled with material 24. Once this has been achieved, the remaining filamentary material 24 could be cut by means of a suitable cutting element located either at the distal end of the catheter 12 or adjacent the dispensing assembly 100.

Figure 5:
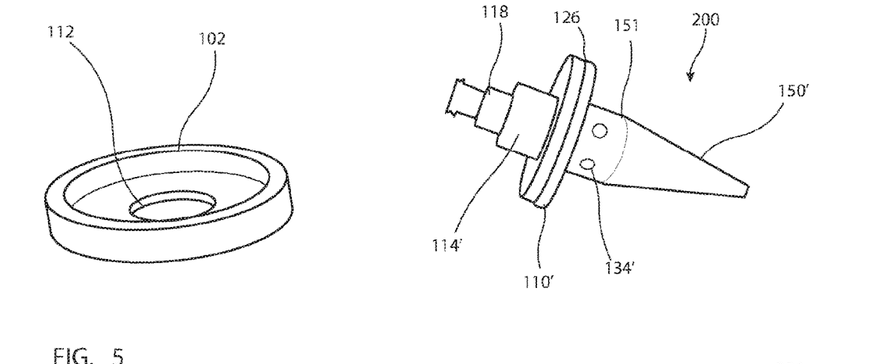
FIG. 5 shows another embodiment of material carrier of the embodiment of FIGS. 2 to 4.

A slightly modified version of the embodiment of FIGS. 2 to 4 can be seen in FIG. 5. The primary difference is that the internal components are formed as a single piece. More particularly, there is provided a material carrier 200 which has at a distal end a conical carrier portion 150' and at a proximal end a cylindrical collar 151 with a plurality of circumferentially spaced apertures 134'. Beyond the collar 151 is a disk-shaped base element 110', from which there extends a coupling collar 114'. The coupling collar 114' has an internal screw thread which co-operates with a male screw threaded element 120 (not visible in FIG. 5) of a male luer connector 118. The O-ring seal 126 is held against the base element 110' and for this purpose the base element 110' may have a raised annular shoulder for supporting the O-ring seal 126, in similar form to the shoulder 124 of the base element 110 of FIG. 2. The material carrier 200 has a fluid passage extending through the connector sleeve 114' and to the apertures 134', such that fluid can pass through the male luer connector 118 to the apertures 134'. The material carrier 200 fits within a casing formed of parts 102, 104 substantially the same as those of the embodiment of FIGS. 2 to 4. The O-ring seal 126 seals the two parts 102, 104 in fluid tight manner to one another, save for the inlet and outlet. The O-ring seal 126 may also prevent rotation of the material carrier 200 within the casing by virtue of a friction fit between the seal 126, the carrier element 200 and the internal walls of the casing parts 102, 104.

The operation of the device with the material carrier 200 is the same as that of the embodiments of FIGS. 2 to 4.

Figure 6:
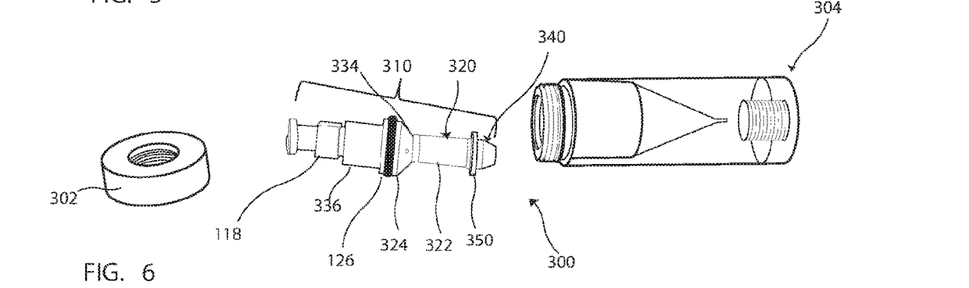
FIGS. 6 and 7 show another embodiment of material carrier.
Figure 7:
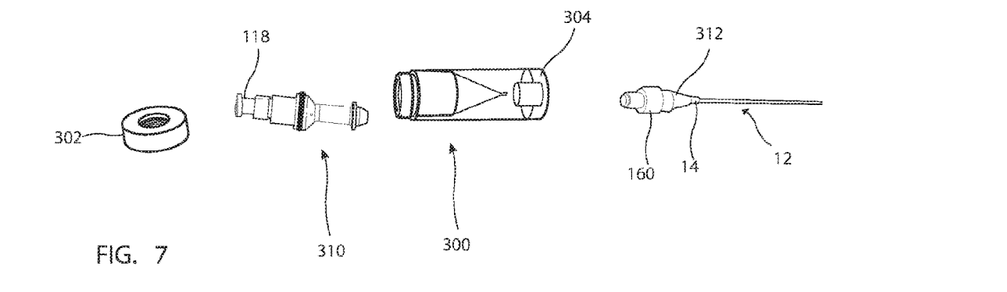
Figure 8:
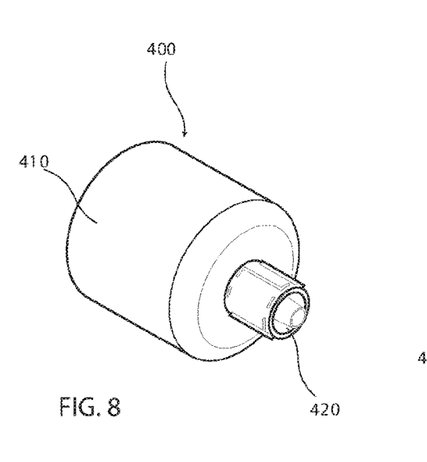
FIGS. 8 to 11 show another embodiment of material receptacle and carrier.
Figure 9:
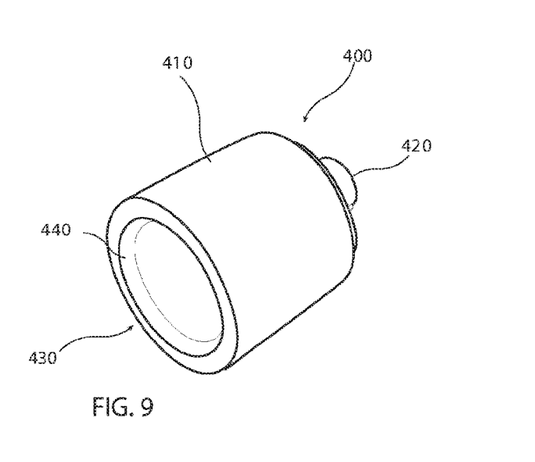
Figure 10:
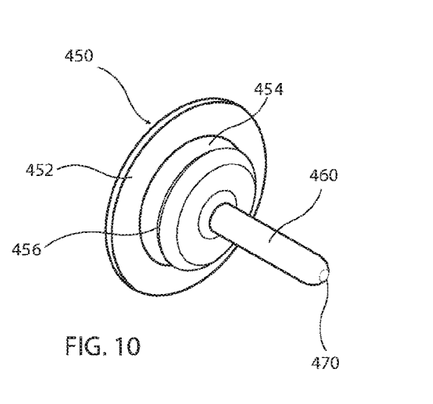
Figure 11:
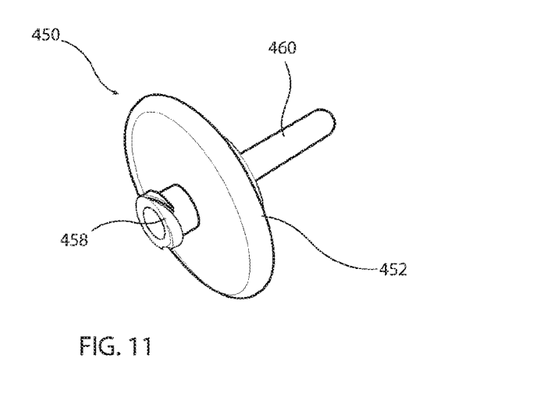
Figure 12:
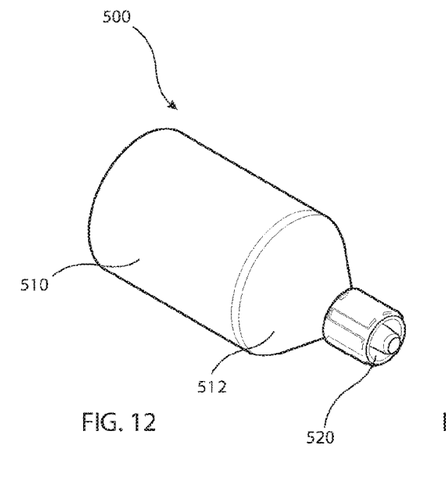
FIGS. 12 to 15 show another embodiment of material receptacle and carrier.
Figure 13:
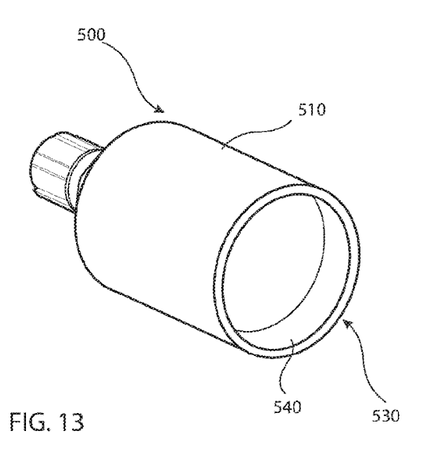

Referring now to FIGS. 6 and 7, this shows another embodiment of dispenser assembly 300 which includes a casing formed of first and second casing parts 302, 304 similar to the casing parts 102, 104 of the previously described embodiments. This embodiment also includes a material carrier assembly 310 which includes a first element 320 having a generally conical material carrier portion 322, a conical base 324 having a plurality of apertures 334 disposed circumferentially therearound, and a connector sleeve element 336 having an internally threaded bore which co-operates with a male threaded connector part of a male luer connector 118. The element 320 also includes at the large end of the conical portion 324 an annular groove therein (not visible in FIGS. 6 and 7) for holding the O-ring seal 126.

At the distal end 340 of the element 320, there is provided an annular guide element 350 which sits within a suitable groove (not visible in FIGS. 6 and 7) of the element 320. The guide 350 is preferably made of a very low friction material, such as PTFE or ePFTE. The guide 350 may be fixed to the element 320 but is preferably able to rotate relative to the element 320. The guide 350 includes a small hole therein (not shown in the drawings) through which the filamentary material can pass. The guide thus assists in feeding the filamentary material to the outlet.

It is to be appreciated that all the embodiments disclosed herein may be provided with a guide similar to guide 350 of the embodiment of FIGS. 6 and 7.

In all other respects, the embodiment of FIGS. 6 and 7 is similar to that of the previously described embodiments, with driving fluid being able to pass through the male luer connector 118 from a source of driving fluid (for example a syringe filled with saline solution) and through the apertures 334 into the chamber of the casing element 304 in order to pull filamentary material into the catheter 12. In this regard, it can be seen in FIG. 7 that the catheter 12 couples to the female connector luer connector 160 by a male luer connector 312 fixed to the proximal end 14 of the catheter 12.

The element 310 may be rotatable within the casing 302, 304 but may equally be non-rotatably fixed therein.

Referring now to FIGS. 8 to 11, these show another embodiment of material holder or receptacle 400 in accordance with the invention. The receptacle 400 includes, in this embodiment, a generally cylindrical body part 410 having an open distal end 430 and a closed flat proximal end which terminates with a female luer fitting 420. The luer fitting 420 couples to an outlet in the closed end of the body part 410 so as to be in fluid communication with the interior chamber of the receptacle 400. The distal end of the receptacle includes an internal annular shoulder 440 for receiving or cooperating with a closure element 452 of the material carrier 450. In the embodiment shown, the closure element 452 is a disc shaped cover of a size conforming to that of the open end of the body part 410 so as to be able to seal the chamber of the receptacle 400. There is provided a raised disc shaped seal holder 454 having an annular groove 456 extending around its periphery for holding an O-ring seal (not shown). The O-ring seal will abut against the inner surface of the body portion 410, preferably at the shoulder 440. The seal holder 454 in this example tapers from the closure element 452, which assists in fitting of the closure element 453 to the body 410.

The outer or exposed side of the closure element 452 has fitted thereto a male luer fitting 458 for coupling to a source of driving fluid, for instance a syringe.

Extending from the centre of the closure element 452 is a material carrier shaft 460, in the form of a cylinder or shaft having a lumen 470 extending throughout its length and in fluid communication with the luer fitting 458. The material carrier shaft 460 has a length shorter than the length of the chamber of the receptacle 400, such that when fitted to the body portion there is a space between the extremity of the material carrier shaft 460 and the outlet from the receptacle chamber.

Filamentary material is wound onto the material carrier shaft 460, preferably in the manner described below, and its second or free end is fed into the outlet of the body portion 410, that is into the lumen leading to the luer fitting 420.

In use, fluid is pumped into the chamber of the receptacle 400 via the inlet luer fitting 458, whereupon it passes through the lumen 470 of the material carrier 450. The chamber of the receptacle 400 will fill with fluid, enveloping the filamentary material wound on the carrier shaft 460, which will make it easier to unwind the filamentary material. The pumped fluid will also pass into the outlet 420, particularly once the chamber has filled with fluid so as to increase pressure in the chamber, and in practice into a delivery catheter attached to the luer fitting 420. This flow of fluid will pull the filamentary material with it, thereby to deliver the filamentary material through the catheter and into the patient.

The lumen 470, which is generally aligned with the outlet 420, also provides a flow of driving fluid directly into the outlet 420 and therefrom into the attached catheter, which contributes to an increased filament driving force.

Referring now to FIGS. 12 to 15, these show another embodiment of material holder or receptacle 500 in accordance with the invention and similar to the embodiment of FIGS. 8 to 11. The receptacle 500 includes, in this embodiment, a generally cylindrical body part 510 having an open distal end 530 and a conical closed proximal end 512 which terminates with a luer fitting 520. The chamber in the receptacle 500 also has a conical proximal end consistent with its outer shape.

The luer fitting 520 couples to an outlet in the closed end of the body part 510 so as to be in fluid communication with the interior chamber of the receptacle 500. The distal end of the receptacle includes an internal annular shoulder 540 for receiving or cooperating with a closure element 552 of the material carrier 550. In the embodiment shown, the closure element 552 is a disc shaped cover of a size conforming to that of the open end of the body part 510 so as to be able to seal the chamber of the receptacle 500. There is provided a raised disc shaped seal holder 554, which may have an annular groove extending around its periphery for holding an O-ring seal (not shown).

The outer or exposed side of the closure element 552 has fitted thereto a male luer fitting 558.

Extending from the centre of the closure element 552 is a material carrier member, comprising a cylinder or shaft 560 and a conical portion 562 adjacent the closure element 552. The conical portion 562 may terminate short of the closure element 552 to leave a narrow connecting neck, as can be seen particularly in FIG. 15. The carrier member has a lumen 570 extending throughout its length and in fluid communication with the luer fitting 558. The material carrier 560/562 has a length shorter than the length of the chamber of the receptacle 500, such that when fitted to the body portion there is a space between the extremity of the material carrier shaft 560 and the outlet from the receptacle chamber.

Filamentary material is wound onto the material carrier shaft 560 and conical portion 562, preferably in the manner described below, and its free or second end is fed into the outlet of the body portion 510, that is into the lumen leading to the luer fitting 520.

In use, fluid is pumped into the chamber of the receptacle 500 via the inlet luer fitting 558, for example by means of a syringe, whereupon it passes through the lumen 570 of the material carrier 550. The chamber of the receptacle 500 will fill with fluid, enveloping the filamentary material wound on the carrier shaft 560 and cone 562, which will make it easier to unwind. The pumped fluid will also pass into the outlet 520, particularly once the chamber has filled with fluid so as to increase pressure in the chamber, and in practice into a delivery catheter attached to the luer fitting 520. This flow of fluid will pull the filamentary material with it, thereby to deliver the filamentary material through the catheter and into the patient.

Figure 14:
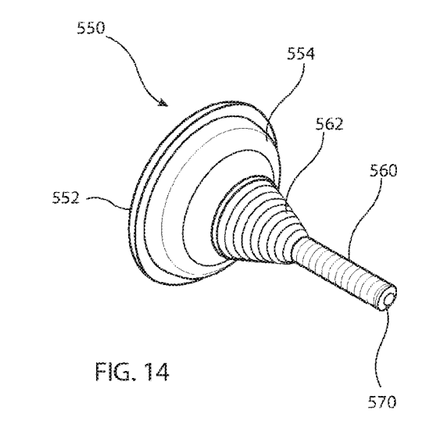
Figure 15:
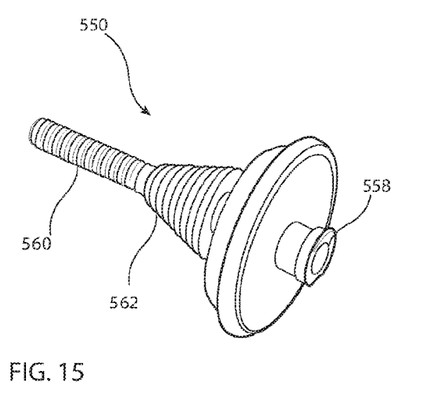

FIGS. 14 and 15 show the surface of the material carrier 550, that is of the conical portion 562 and the cylindrical shaft portion 560 being stepped. In other embodiments, these surfaces could be smooth.

The lumen 570, which is generally aligned with the outlet 520, also provides a flow of driving fluid directly into the outlet 520 and therefrom into an attached catheter, which contributes to an increased filament driving force.

It is to be understood that the embodiments of FIGS. 3 to 7 could have a material carrier with a lumen extending along its length similar to the embodiments of FIGS. 8 to 14, and similarly the embodiments of FIGS. 8 to 15 could have driving fluid conduits and apertures exiting laterally adjacent the distal end of the material carrier in manner similar to the embodiments of FIGS. 3 to 7.

Figure 16A:
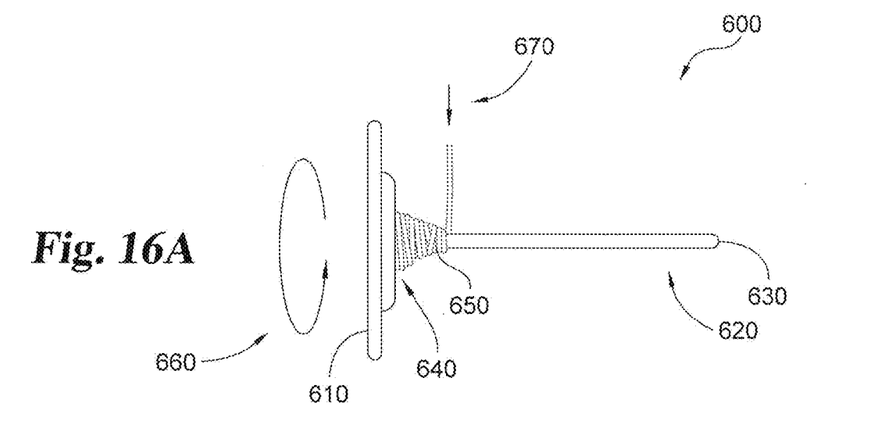
FIGS. 16A to 16C show a preferred embodiment of material winding method for winding filamentary material onto a carrier.
Figure 16B:
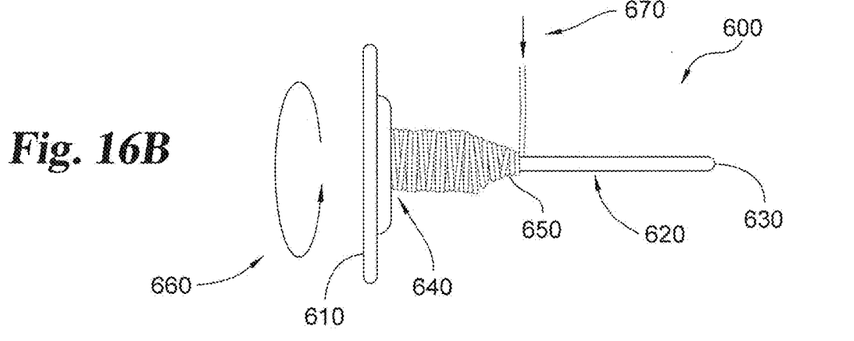
Figure 16C:
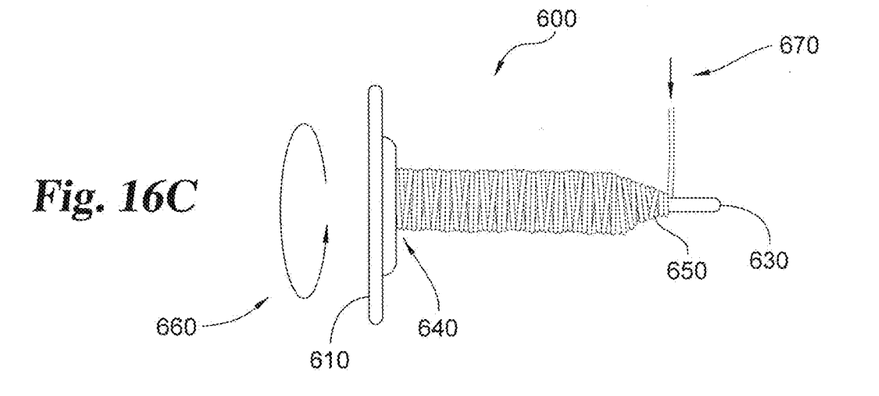

FIGS. 16A to 16C show a preferred embodiment of winding process for winding filamentary material, or thread, onto the material carrier. The method depicted and disclosed herein is suitable for all embodiments disclosed herein and covered by the scope of the claims.

Referring first to FIG. 16A, this shows in schematic form a material carrier 600 similar to that of the embodiment of FIGS. 8 to 11, although it could be any other material carrier including a conical carrier of the type shown in FIGS. 3 to 5 or part conical carrier of the type shown in FIGS. 14 and 15. In the example shown, the material carrier 600 includes a receptacle fixing or cover element 610 for attachment to the body portion of a receptacle (not shown) and a shaft 620 which in this embodiment has a lumen (not shown) passing throughout its length and exiting at the tip 630.

Filamentary material 650 is wound onto the shaft 620 commencing from its distal end 640, by rotating the material carrier 600 in the direction of the arrow 660. In the first instance, a few turns of material 650 are wound at the distal end 640 and then the material feed 670 is moved slightly forwards, towards the proximal end 630 of the shaft 620, by a given amount. So doing creates a conical layer of material 650. The material feed 670 is reciprocated backwards and forwards to form a series of conical layers of material 650, winding over the first turns, and once the desired diameter of wound material 650 is reached at the distal most position on the shaft 620, the material feed 670 is moved proximally by a given distance, that is towards the proximal end 630, typically equivalent to around one or more thread widths, to wind another conical layer of material 650 over the conical base already formed. The material feed 670 is moved gradually towards the proximal end 630 in stages while reciprocating backwards and forwards by a given distance, so as to create a series of overlapping conical layers of material 650 extending towards the proximal end 630, as can be seen in the sequence shown in FIGS. 16A to 16C. The conical layers of material 650 will in practice be distinct from one another in terms of winding sequence. As a result, when the material 650 is made to unwind from the carrier 600 it will do so one conical section at a time. Thus only the proximal most portion of filamentary material 650 or thread will unwind, even though there are in practice many layers of material 650 carried on the carrier 600. When the first conical layer has been unwound, the next in the series will unwind. This arrangement can prevent unwinding from outer layers distal of the proximal end of the winding, which can cause turns of material to become embedded in underlying layers during the unwinding process. Any such embedding of the thread, as can occur in prior art arrangements, can lead to increased resistance to unwinding and at worst blockage of the thread on the carrier 600. Similarly, this arrangement can ensure that no turns of thread uncouple prematurely from the shaft 620.

The material feed 670 could be any suitable element, including a movable feed nozzle or guide attached to a material supply. Control of the material feed could be mechanical and/or electronic as desired.

It will be appreciated that the thread 650 will be pulled from the distal end 630 in a direction precisely parallel or substantially parallel to the axis of the shaft 620 in the embodiments disclosed herein.

Figure 17A:
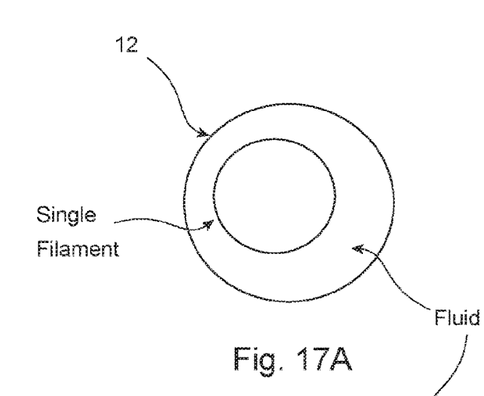
FIGS. 17A to 17C show in schematic form a catheter in transverse cross-section with one or more filaments of bioabsorbable material held therein.
Figure 17B:
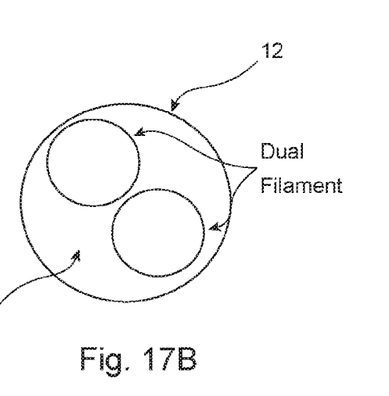
Figure 17C:
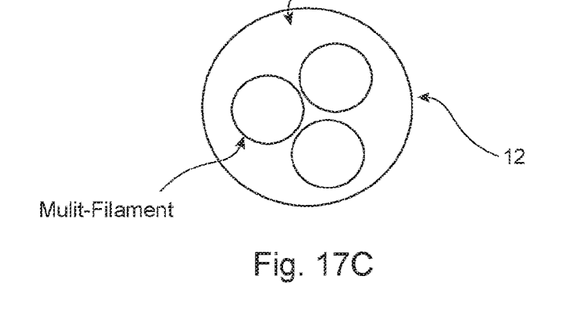

Referring now to FIGS. 17A to 17C, these show in schematic form a catheter 12 in transverse cross-section with one or more filaments of bio absorbable material 24 held therein. The current goal of the device is to introduce bioabsorbable material in the form of a filament into the cavity of an aneurysm. It is postulated that the material will initially create an embolic reaction within the cavity of the aneurysm, before acting as a scaffold to engender cellular growth. The filament 24 itself is constrained in size to fit within the lumen of the catheter 12 to enable delivery. When coming into contact with the blood, cells will permeate the material 24 and the expectation is that the material will remodel over time into natural tissue. If sized correctly, it is possible to introduce more than one filament at the same time through the lumen of the catheter 12. The introduction of multi-filaments instead of a single filament, as shown in FIGS. 17B and 17C would aid the following:

1) increased contact (surface area) between the filament and the blood to aid thrombogenicity;

2) slight separation of the filaments upon exiting the aneurysm may help distribute the material evenly;

3) less fluid required to deliver the filament in longer lengths, albeit in smaller volumes;

4) it will also be appreciated that in the embodiments disclosed, the material is wound onto a carrier which is substantially aligned with the longitudinal axis of the dispenser and of the apparatus itself. In practice, the long axis of the material carrier is at least roughly in the dispensing direction of the assembly.

In the preferred embodiments, the carrier element is precisely aligned with the dispensing direction of the receptacle. In other embodiments, the carrier element may be disposed at an angle to the dispensing direction of the receptacle. In such embodiments, the carrier will have a side relatively remote from the outlet of the receptacle and thus to the dispensing direction. This angle is advantageously no more than around 30 degrees relative to the dispensing direction, in practice the longitudinal axis of the receptacle as determined by the direction of movement of the fibre out of the outlet. More suitably, this angle is less than around 20 degrees and even more suitably less than around 10 degrees. In practice, the angle should preferably be less than around 5 degrees. It will be appreciated that in embodiments having a cylindrical carrier element, both the closer and the remote side of the carrier when in the angled disposition will be at the same angle to the dispensing direction. On the other hand, in cases where the carrier is not cylindrical, for instance is conical as shown in some embodiments, the side of the carrier closer to the outlet may be at a greater angle than that of the side remote from the outlet. The term "substantially aligned" as used herein in relation to the relationship of the carrier relative to the dispensing direction is therefore to be understood to encompass one of these preferred ranges, as well as an arrangement in which the carrier is precisely aligned with the dispensing direction.

The delivery systems taught herein functions when a fluid is introduced within the catheter 12 dragging the filament 24 along its lumen. A small but minimum fluid velocity is required to generate enough friction to drag the filament 24, thereby making the applied force by the user (for example with a syringe) a relevant element in its operation. While no patient risk is perceived by applying a force too small to enable the system to work, the function of the pressure valve will enhance the system as:

1) it will prevent the user from introducing excess liquid into the aneurysm without any advancement of the material;

2) it will provide tactile feedback to the user as the valve will prevent liquid from exiting the syringe without the application of a minimum force, giving the user 'feel' when operating the device.

An example of a minimum pressure valve arrangement is shown in FIGS. 18A to 20B, in which it can be seen that a valve 55 is disposed at the inlet to the receptacle 30. The valve 55 itself can be made from any suitable material, such as a polymer or rubber. Silicone is a particularly suitable material due to its mechanical properties.

As depicted in the Figures, the optimal shape of the valve 55 is a dome which is split into a number of leaves or elements 57 (four leaves in this example), and a disc 59 at the base which functions as an anchor to fix the valve 55 within the receptacle 30.

Figures 18A, 19A:
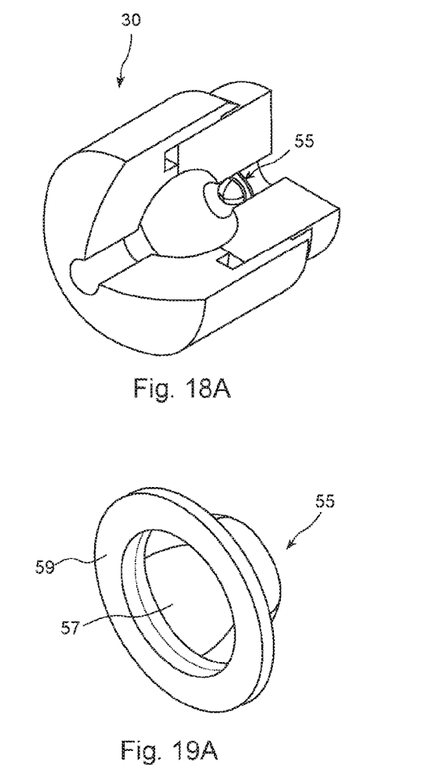
FIGS. 18A and 18B are perspective views of an example of receptacle including a minimum fluid pressure valve.
FIGS. 19A and 19B are perspective views of the valve in FIGS. 13A and 13B in a closed condition.
Figures 18B, 19B:
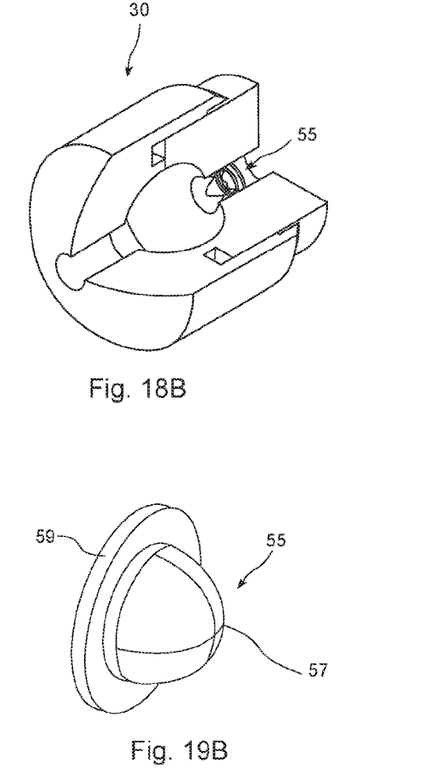
Figure 20A:
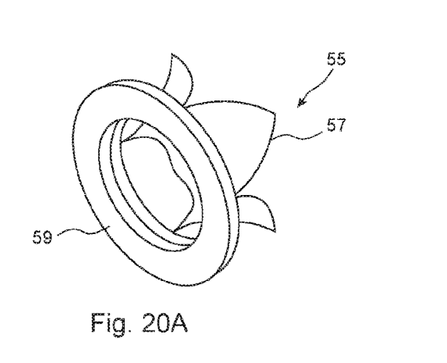
FIGS. 20A and 20B are perspective views of the valve in FIGS. 13A and 13B in an open condition.
Figure 20B:
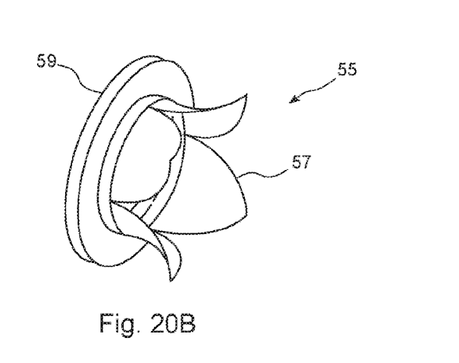

FIGS. 18B, 20A and 20B show the valve 55 when sufficient fluid force is applied. The capacity of the valve 55 to open will be determined by the choice of material and wall thickness. The valve 55 will return to its natural closed position, as seen in FIGS. 18A, 19A and 19B, when the force applied (by the syringe) becomes too small to keep the leaves 57 open.

The valve 55 is preferably positioned at the proximal end of the receptacle, between the syringe connection and the main chamber.

In the embodiments described the filamentary material is fed through a catheter into the patient. It is to be understood that the teachings herein are not limited to a specific deliver device and could be used with any tubular delivery device including a catheter, cannula or needle.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

What is claimed is:

1. An apparatus for delivering filamentary material into a patient, the apparatus comprising:
    a tubular delivery element having a proximal end, a distal end and a lumen extending within the tubular delivery element from the proximal to the distal ends;
    a material receptacle having an aperture for receiving driving fluid into the receptacle, and an outlet coupled to the lumen of the tubular delivery element, the outlet extending in a material dispensing direction of the receptacle; and
    a carrier element for carrying filamentary material, the carrier element having an axis substantially aligned with the material dispensing direction of the receptacle and including a body portion around which filamentary material can be wound.

2. The apparatus according to claim 1, wherein the tubular delivery element includes at least one of a catheter, a cannula and a needle.

3. The apparatus according to claim 1, wherein the carrier element is precisely aligned with the dispensing direction of the receptacle.

4. The apparatus according to claim 1, wherein the carrier element is disposed at an angle to the dispensing direction of the receptacle, wherein a side of the carrier element relatively remote from the outlet is disposed at an angle of no more than around 30 degrees.

5. The apparatus according to claim 4, wherein the side of the carrier element relatively remote from the outlet is disposed at an angle of no more than around 10 degrees.

6. The apparatus according to claim 4, wherein the side of the carrier element relatively remote from the outlet is disposed at an angle of no more than around 5 degrees.

7. The apparatus according to claim 1, wherein the body portion of the carrier element is generally round in transverse cross-section.

8. The apparatus according to claim 1, wherein the body portion of the carrier element is fixed to the receptacle so as to be immovable relative thereto.

9. The apparatus according to claim 8, wherein the body portion of the carrier element includes a generally conical portion.

10. The apparatus according to claim 9, wherein the body portion of the carrier element includes a generally cylindrical portion extending longitudinally beyond a narrow end of the conical portion.

11. The apparatus according to claim 1, wherein the body portion of the carrier element has a generally conical form tapering in a direction towards the outlet.

12. The apparatus according to claim 11, wherein at least a part of the body portion of the carrier element is conical.

13. The apparatus according to claim 1, wherein the body portion of the carrier element includes a generally cylindrical portion.

14. The apparatus according to claim 1, wherein the body portion of the carrier element includes a conical portion and a generally cylindrical portion extending longitudinally beyond a narrow end of the conical portion.

15. The apparatus according to claim 1, wherein the carrier element includes at least one driving fluid conduit.

16. The apparatus according to claim 15, wherein the at least one conduit includes at least one aperture disposed at an end of the carrier element furthest from the receptacle outlet.

17. The apparatus according to claim 1, wherein the receptacle includes a tapering internal wall adjacent the outlet.

18. The apparatus according to claim 1, including a guiding element at an end of the material carrier closest to the outlet.

19. The apparatus according to claim 18, wherein the guiding element includes a hole for the passage of filamentary material therethrough.

20. The apparatus according to claim 1, including filamentary material carried on the material carrier.

21. The apparatus according to claim 20, wherein the filamentary material carried on the material carrier includes one or more of: SIS, polysaccharide, a biocompatible polymeric thread or other biocompatible material.

22. The apparatus according to claim 20, wherein the filamentary material carried on the material carrier includes one or more of: woven polyester, polyamide, expanded polytetrafluoroethylene; bioremodelable materials such as: extracellular matrix material including submucosa, renal capsule membrane, dermal collagen, dura mater, pericardium, fascia lata, serosa, peritoneum and basement membrane layers.

23. The apparatus according to claim 20, wherein the filamentary material is wound on the material carrier from a distal end thereof to a proximal end thereof, the proximal end being closest to the outlet.

24. The apparatus according to claim 23, wherein at least a part of the filamentary material is wound on the material carrier in sections from the distal end to the proximal end.

25. The apparatus according to claim 20, wherein at least a part of the filamentary material is wound in conical layers on the carrier.

26. The apparatus according to claim 20, further comprising a catheter.

27. The apparatus according to claim 26, wherein the filamentary material has a diameter that is a close fit within the catheter.

28. The apparatus according to claim 1, wherein the receptacle is at least partially transparent or translucent.

29. The apparatus according to claim 1, including a fluid supply and pump for pumping driving fluid into the receptacle.

30. An apparatus comprising:
    a tubular delivery element having a proximal end, a distal end and a lumen extending within the tubular delivery element from the proximal to the distal ends;
    a material receptacle having an aperture for receiving driving fluid into the receptacle, and an outlet coupled to the lumen of the tubular delivery element, the outlet extending in a material dispensing direction of the receptacle;
    a filamentary material; and
    a carrier element carrying the filamentary material, the carrier element having an axis substantially aligned with the material dispensing direction of the receptacle and including a body portion around which filamentary material is wound;

wherein the filamentary material is wound on the material carrier from a distal end thereof to a proximal end thereof, the proximal end being closest to the outlet;

wherein at least a part of the filamentary material is wound on the material carrier in sections up to a maximum wound diameter on the material carrier from the distal end to the proximal end.

31. An apparatus for delivering filamentary material into a patient, the apparatus comprising:
- a tubular delivery element having a proximal end, a distal end and a lumen extending within the tubular delivery element from the proximal to the distal ends;
- a material receptacle having an aperture for receiving driving fluid into the receptacle, and an outlet coupled to the lumen of the tubular delivery element, the outlet extending in a material dispensing direction of the receptacle;
- a carrier element for carrying filamentary material, the carrier element having an axis substantially aligned with the material dispensing direction of the receptacle and including a body portion around which filamentary material can be wound;

wherein the body portion of the carrier element is fixed to the receptacle so as to be immovable relative thereto; and
- a sleeve positioned between the aperture and the carrier element, wherein the sleeve is fluidly coupled to the aperture, and wherein the sleeve defines a plurality of apertures disposed circumferentially around the sleeve.

32. The apparatus according to claim 31, wherein the sleeve and the carrier element are formed as a single piece.

33. The apparatus according to claim 31, wherein the body portion of the carrier element is generally round in transverse cross-section.

34. The apparatus according to claim 31, wherein the body portion of the carrier element is fixed to the receptacle so as to be immovable relative thereto.

35. The apparatus according to claim 31, wherein the body portion of the carrier element has a generally conical form tapering in a direction towards the outlet.

36. The apparatus according to claim 35, wherein at least a part of the body portion of the carrier element is conical.

37. The apparatus according to claim 31, wherein the body portion of the carrier element includes a generally cylindrical portion.

38. The apparatus according to claim 31, wherein the body portion of the carrier element includes a conical portion and a generally cylindrical portion extending longitudinally beyond a narrow end of the conical portion.

39. The apparatus according to claim 31, wherein the carrier element includes at least one driving fluid conduit.

40. The apparatus according to claim 39, wherein the at least one conduit includes at least one aperture disposed at an end of the carrier element furthest from the receptacle outlet.

41. The apparatus according to claim 31, wherein the receptacle includes a tapering internal wall adjacent the outlet.

42. The apparatus according to claim 31, including a guiding element at an end of the material carrier closest to the outlet.

* * * * *